(12) United States Patent
Scofield (10) Patent No.: US 6,443,010 B1
(45) Date of Patent: Sep. 3, 2002

(54) AUDIBLE AIR FLOW DETECTOR FOR AIR FILTERS

(75) Inventor: William Harold Scofield, Lombard, IL (US)

(73) Assignee: Lucent Technologies Inc., Murray Hill, NJ (US)

( * ) Notice: Subject to any disclaimer, the term of this patent is extended or adjusted under 35 U.S.C. 154(b) by 0 days.

(21) Appl. No.: 09/464,920

(22) Filed: Dec. 16, 1999

(51) Int. Cl.[7] .............................................. G01N 29/00
(52) U.S. Cl. .............................. 73/587; 73/591; 73/645
(58) Field of Search ........................ 73/587, 591, 592, 73/645, 649; 340/606, 607

(56) References Cited

U.S. PATENT DOCUMENTS

| | | | | |
|---|---|---|---|---|
| 3,668,887 A | * | 6/1972 | Riello | 62/262 |
| 4,205,904 A | * | 6/1980 | Skubich et al. | 340/631 |
| 5,434,644 A | * | 7/1995 | Kitano et al. | 355/30 |
| 5,461,368 A | * | 10/1995 | Comer | 340/607 |
| 5,774,056 A | * | 6/1998 | Berry, II et al. | 340/607 |
| 5,850,183 A | * | 12/1998 | Berry, III | 340/607 |
| 5,914,453 A | * | 6/1999 | James et al. | 95/14 |

* cited by examiner

Primary Examiner—Hezron E. Williams
Assistant Examiner—Jacques Saint-Surin
(74) Attorney, Agent, or Firm—Grossman, Patti & Brill

(57) ABSTRACT

An apparatus for detecting blockage of a porous medium of an air filter utilized to filter air within a forced air stream contained within an enclosure. The air filter extends in a direction transverse to a direction of the forced air stream. The detection is accomplished with an opening in the porous medium of a greater dimension than provided by the porous medium. The opening is defined by the porous medium of the air filter and extends through the porous medium through which airflow from the forced air stream passes. A flexible member is provided which is positioned within the air flow from the forced air stream which passes through the opening and received by the flexible member causing the flexible member to vibrate and emit an audible sound in response to the air flow. Additionally, a method is provided for detecting blockage of the porous medium of the air filter including the steps of providing an opening in the porous medium; selecting a flexible member in which the flexible member vibrates emitting a desired audible sound with the flexible member positioned to receive a flow of air at a particular velocity; and positioning at least a portion of the flexible member in communication with the opening in the porous medium to receive the air flow from the forced air stream.

35 Claims, 4 Drawing Sheets

AUDIBLE AIR FLOW DETECTOR FOR AIR FILTERS

TECHNICAL FIELD

This invention relates generally to air filters utilized in forced air streams and, more particularly, to the detection of debris trapped in the air filter for purposes of changing the air filter.

BACKGROUND OF THE INVENTION

It is known that forced air filters are used to trap and remove undesirable debris and particles from a forced air stream. There are numerous applications and uses for such filtered forced air streams. A common use of a forced air stream includes conventional heating, air conditioning and ventilation (HVAC) systems utilized in residential and commercial buildings. Other similar applications or uses include providing controlled air supplies to particular rooms or confinements which contain activities such as manufacturing processes, assembling activities, electronic equipment and components which are sensitive to various air borne debris and need to be in a controlled air environment.

In the operation of these forced air streams, a filter is generally positioned in the path of the air stream contained in an enclosure, conduit or duct of an air system. The forced air stream carrying the debris strikes the filter on an upwind side of the filter and the filter traps the debris within its filter structure. The filter structure includes a porous medium which permits forced air through the filter and traps debris and particles. The porous medium often is pressed paper utilized in residential HVAC systems while polyester fibers are used in more commercial and industrial HVAC systems, however other common porous medium are used.

The trapped debris remains in the filter structure and the air stream passes through the filter and exits the filter on the downwind side absent the debris once carried by the forced air stream. As more air passes through the filter, more debris is trapped by the filter. As the filter becomes more burdened with the debris removed from the forced air stream, the filter becomes more blocked not permitting the air stream to readily pass through the filter as efficiently and effectively as it previously did with less debris trapped within the filter.

Typically the porous medium of the central portion of the filter receives the higher velocity and greater volume of air than the porous medium nearer the edges of the filter which are more proximate to the enclosure or conduit which contains the forced air stream. As a result, the central portion of the porous medium will tend to clog up and be blocked more quickly than the outer edges of the porous medium of the filter which receives less volume of air and therefore typically less debris.

A filter which is overly burdened with debris will cause back pressure on the air stream and will reduce the air supply to the desired destination of the air stream. Additionally, a more burdened filter is more likely to dislodge previously trapped debris and diminish the effectiveness of the filter. Thus, an overburdened air filter will diminish the air flow and at the same time, increase the debris content within the air stream downstream of the air filter. This will result in jeopardizing the comfort and health of the recipients or the operation of certain sensitive equipment and processes which receive such air stream.

As a result, the air filters that are in operation within the air stream must be monitored for replacement. This monitoring is typically accomplished by periodic visual inspection, and in other instances, the filters are merely automatically replaced at predetermined time intervals. Neither of these approaches are in response to the actual condition or debris content of the air filter. Additionally, the former is labor intensive and may require several visual inspections before replacement would be warranted. Moreover, the latter is somewhat arbitrary in that the forced air streams containing debris may vary over time in their content of debris and volume of air and therefore result in the filters being replaced either prematurely or too late.

SUMMARY OF THE INVENTION

The problems noted above are solved in accordance with the apparatus of the present invention which provides a device which provides an audible alert sound indicating the air filter has become overly burdened with debris thereby alerting the maintenance personnel to replace the overly burdened and ineffective air filter. The audible alert sound enables the maintenance personnel to replace the filter at a time when the blockage of the filter has actually occurred and alleviates time consuming periodic visual inspections or the inefficiencies created by arbitrary automatic replacement of the air filter at predetermined time intervals.

In accordance with the present invention a method is also provided to provide an audible alert sound to indicate to the maintenance personnel that the air filter is overly burdened with debris and needs replacement. This audible alert sound is provided at a time when the undesirable loading of the filter has actually occurred. The method enables the maintenance personnel to reduce the number of visual inspections and the time associated with such inspections. Additionally, the air filters can now be replaced at a time when the air filter is actually overly burdened and undesirably less effective for the subject air stream.

BRIEF DESCRIPTION OF THE DRAWINGS

The foregoing advantageous features of the invention will be explained in greater detail and others will be made apparent from the detailed description of the present invention which is given with reference to the several figures of the drawing, in which.

DETAILED DESCRIPTION

Figure 1:
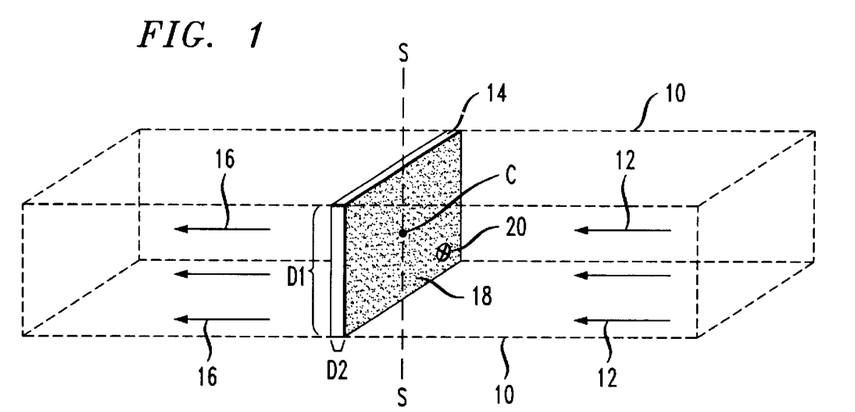
FIG. 1 is a perspective view of an air filter which carries the invention positioned within an enclosure, in phantom, containing a forced air stream.

Referring to FIG. 1, an enclosure, conduit or duct 10 of a heating, ventilation and air conditioning system (HVAC), is shown in phantom, which contains forced air stream 12, indicated by arrows, upstream from air filter 14. The air stream downstream from air filter 14 is indicated by arrows 16. Air stream 12 typically carries debris and particles that need to be removed by air filter 14 in order to cleanse the downstream air stream 16 that moves away from air filter 14 and is received at a location which requires the clean air.

Air filter 14 is typically constructed with porous medium 18 which will trap the undesirable debris and particles of forced air stream 12 and permit cleansed air 16 to pass downstream from air filter 14. There are various constructions of porous medium 18 depending on the intended environment of use. For example, pressed paper is often used for air filters utilized in a residential HVAC system where the flow rates are typically 250 cfm to 300 cfm and could go to 800 cfm. On the other hand, a more durable polyester fibrous fabric would be used for porous medium 18 which may be used with a wire mesh overlying the porous medium 18 in a more harsh environment of a commercial or industrial HVAC system where the flow rate could be 100,000 cfm.

Air filter 14 is generally positioned across the entire path of forced air stream 12 and in a transverse direction to the forced air stream 12, as seen in FIG. 1. This will assure that forced air stream 12 will be filtered by filter 14 and will not significantly escape around the air filter 14 carrying undesirable debris downstream. Moreover, air filters 14 are generally greater in a dimension D1 which is transverse to the direction of the forced air stream 12 than a dimension D2 of air filter 14 in direction of forced air stream 12, as seen in FIG. 1.

The present invention includes opening 20 in porous medium 18 which is greater in dimension than smaller openings which the porous medium 18 will provide for the filtering process. Opening 20 is defined by the porous medium 18 and extends through air filter 14 as seen in FIGS. 3 and 4 and extends in a direction along that of forced air stream 12, as seen in FIGS. 1, 3 and 4.

Figure 2:
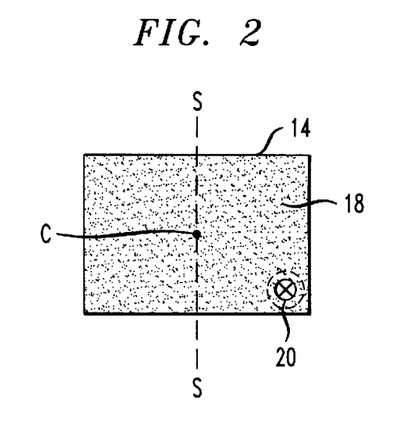
FIG. 2 is a front elevational view of the air filter in FIG. 1.
Figure 3:
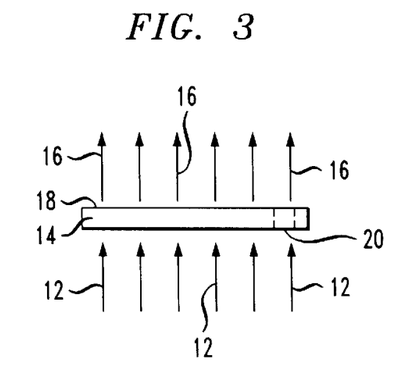
FIG. 3 is a top view of a clean air filter of FIG. 2 without a portion of the invention.
Figure 4:
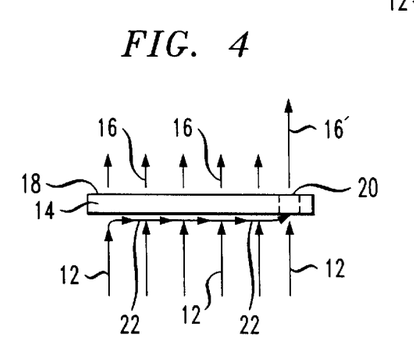
FIG. 4 is a top view of a debris burdened air filter of FIG. 2 without a portion of the invention.

FIGS. 2, 3 and 4 will be discussed in connection with one another as to the dynamics of forced air stream 12 and the positioning of opening 20 in filter 14. It should be noted that FIGS. 3 and 4 do not contain a portion of the invention within opening 20 and are utilized more for demonstrating the drawings of air flow with filter 14. In viewing FIG. 3, it should be noted that forced air stream 12 will have an oncoming velocity to air filter 14 and with the blockage that clean filter 14 creates in conduit 10, the outcoming or downstream forced air stream 16 will naturally be at an elevated or higher velocity than the oncoming velocity of forced air stream 12. This is derived based on the conservation of energy and momentum on either side of filter 14 from basic principals of Bernoulli's Equation set forth below.

Thus, generally the oncoming velocity of forced air stream 12 will pass through the porous medium 18 of filter 14 and debris will be trapped in porous medium 18 while allowing air to pass through the porosity of the material. The air will exit porous medium 18 passing through smaller openings and the outgoing air stream 16 will be at a higher velocity as the oncoming air stream 12. As blockage from the accumulating debris increases in filter 14, as demonstrated in FIG. 4, the oncoming air stream 12 does not readily pass through the filter and air, represented by arrows 22, moves along the surface of the porous medium 18 and reaches opening 20. When this air reaches opening 20, air 22 passes through opening 20 at a substantially elevated velocity represented by arrow 16'. Thus, the conservation of momentum and energy of the system are generally maintained by having a higher velocity of air and therefore a correspondingly higher volume of air pass through opening 20 of blocked filter 14.

It should be further understood that the oncoming air stream 12 to air filter 14 is not necessarily uniform in velocity across a cross section of conduit 10 as it moves through conduit 10. Generally fluids such as air will be slowed down by the frictional resistance that the sidewalls of conduit 10 that will be imparted to the moving air stream. Thus, you will experience a relatively higher velocity and therefore higher volume of air passing through a central portion of conduit 10 than you will experience near the sidewalls of conduit 10. Because of this phenomenon, generally a greater volume of air will pass through the central portion of clean air filter 14. As a result, the blockage will generally buildup sooner in the central portion of the air filter 14 than the areas more peripheral to air filter 14.

Since opening 20 is part of the invention and locates the position of the invention for detecting of blockage of filter 14, it is well advised for opening 20 to not be placed in a central portion of filter 14. If opening 20 is positioned in a central portion of air filter 14, the detection of blockage in air filter 14 will tend to be premature since the build up of debris will first occur in the central portion of air filter 14. As a result, it is desirable to position opening 20 closer to an edge of filter 14 than a central portion of filter 14. In the instance of a symmetrically shaped filter 14, one that has an axis of symmetry S in a direction transverse to forced air stream 12, as seen in FIGS. 1 and 2, it is preferred to position opening 20 closer to an edge of filter 14 than to center C positioned along and on the axis of symmetry S.

Figures 5, 6:
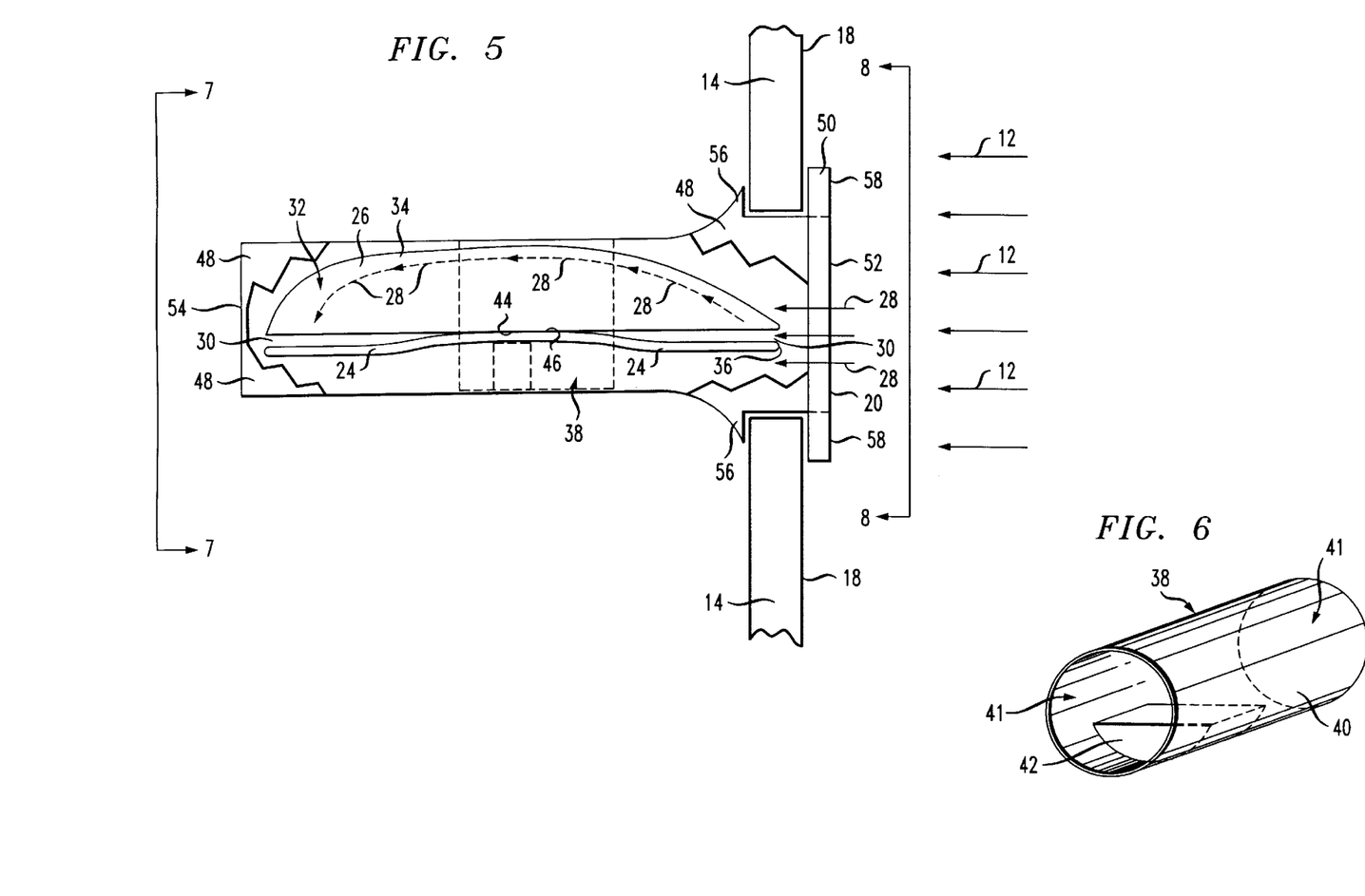
FIG. 5 is an enlarged side elevational view of the apparatus of the present invention with the housing member partially broken away, the porous medium of the air filter partially broken away and cylindrical housing of securement member in phantom.
FIG. 6 is an enlarged perspective view of the securement member for securing the flexible and other members in fixed relationship to one another without the flexible and other members shown.

Referring to FIG. 5, a flexible member 24 is positioned to overlie another member 26. These members are commonly referred to as a reed. Flexible member 24 is often referred to as the tongue of the reed in which at least a portion of tongue 24 will vibrate in response to the flow of air that is passing through opening 20 thereby creating an emission of sound. At a certain velocity flexible member 24 will emit a desired audible sound. A detailed discussion will be made below that will go over the design of or selection of the size and composition of flexible member or tongue 24 such that it will emit a certain desired sound at a certain velocity of air flow indicating a certain level of blockage of air filter 14. Typically, the softer the construction of tongue 24, the more responsive tongue 24 will be to emitting sound for relatively lower velocities of air flow through opening 20 and correspondingly the stiffer the construction of tongue 24, the less responsive tongue 24 will be to emitting sounds from relatively lower air flow velocities that pass through opening 20 and will emit sounds at relatively higher air flow velocities.

In referring to FIG. 5, forced air stream flows toward filter 14 and air flows through opening 20 and encounters flexible and other members 24, 26 in which at least a portion of flexible and other members 24, 26 are in alignment with the air flow, indicated by arrows 28, from forced air stream 12 passing through opening 20. A more detailed discussion of selecting and designing dimensions and composition of the flexible member 24 will be done below.

Figure 11:
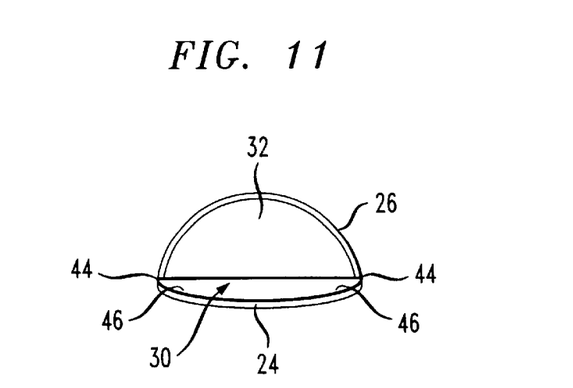
FIG. 11 is the cross sectional view as seen along 11—11 in FIG. 10.

Flexible member 24 preferably is an elongate member which has a longer dimension which extends in the direction of forced air stream 12 than a dimension of flexible member 24 which extends in the plane of the air filter 14 transverse to forced air stream 12. The cross section of flexible member 24 which extends in a plane of air filter 14 and transverse to forced air stream 12 will generally be rectangular in shape as seen in FIG. 11. However, other cross sectional shapes are contemplated. The composition of flexible member or tongue 24 can be made from a number of materials. However, it may be preferable to include durable materials such as brass, aluminum, stainless steel, or bronze which are more resistant to corrosion yet will provide the desired characteristics of vibration of tongue 24. Other member 26 can be made of the same or different material, but is not needed for the dynamic vibration as tongue 24.

Figure 7:
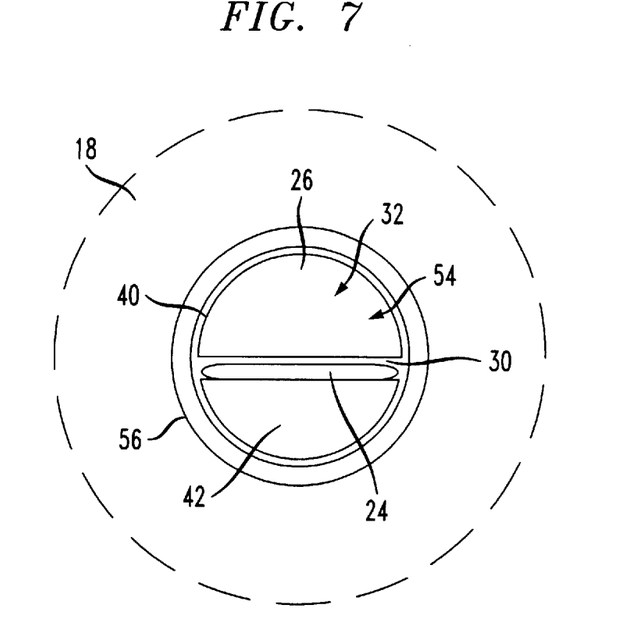
FIG. 7 is an elevational view of the apparatus of the present invention as seen along line 7—7 in FIG. 5.

In referring to FIG. 5, other member 26 generally extends along the dimension of flexible member 24. Members 24, 26 are spaced apart from one another, at least at each end of the elongated flexible member 24 and along at least the length of flexible member 24. Space 30, as seen in FIGS. 5–7, positioned at the end and between the flexible member 24 and other member 26, as seen in FIGS. 5 and 7–11, and is positioned transverse to the direction of forced air stream 12 permitting air flow 28 to enter between the flexible member 24 and other member 26 and move between members 24, 26.

Figure 10:
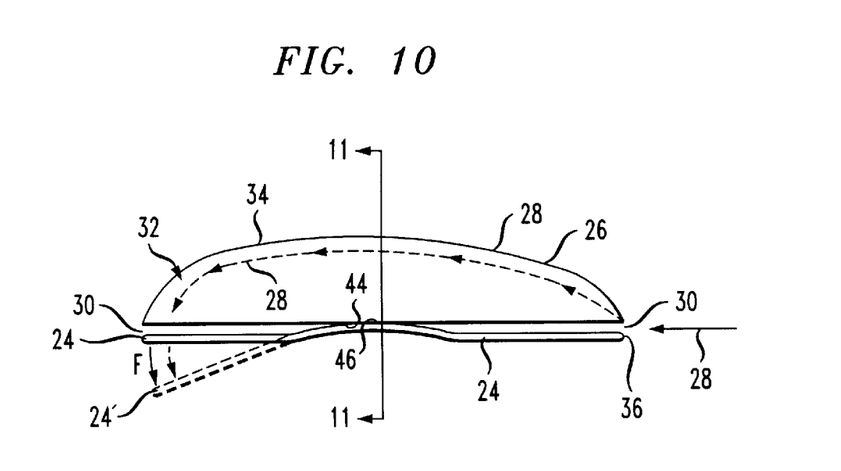
FIG. 10 is an enlarged side elevational view of the reed apparatus alone as seen in FIG. 5 with a showing of the deflection of the tongue in phantom.

Other member 26, has a concave portion 32 defined within member 26, as seen in FIGS. 5, 7, 10 and 11. Concave portion 32 has its opened portion facing flexible member 24, as seen in FIGS. 5, 10 and 11. This concave portion 32, receives air flow 28 which enters opening 30 between the flexible and other members 24, 26 and directs air flow, as seen by arrows 28 along the sidewall 34 of concave portion 32 and directs it in a direction transverse to flexible member 24 impacting flexible member 24, as seen in FIGS. 5 and 10. This concave portion 32 of other member 26 forces air flow 28 to impact the flexible member 24 downstream from a front end 36 of flexible member 24, as seen in FIG. 10. The impacting air flow 28 upon flexible member or tongue 24, if sufficiently forceful enough, will push flexible member 24 apart from other member 26, deflecting flexible member 24 to a deflected position 24' as seen in FIG. 10.

This deflection force once overcome by the resiliency of flexible member 24 begins flexible member 24 to vibrate causing a cycling between low air pressure between other portion 26 and flexible member 24 with the flexible member deflected to 24' away from other member 26. Relatively high air pressure will occur between members 24, 26 when flexible member 24 is undeflected and returns back toward a position more proximate to other member 26. This cycling of high and low air pressure initiates a sound wave. A detailed discussion of correlating a sound wave to a blockage in air filter 14 will be set forth below.

To have this flexible member 24 free to vibrate at this downstream end of flexible member 24, flexible member 24 needs to be secured with securement member 38 upstream from that end position, as seen in FIGS. 5 and 6. Securement member includes a generally cylindrical housing 40, as seen in FIGS. 5 and 6. This cylindrical housing 40 has a platform 42 secured therein upon which a portion of flexible member 24 may rest and other member 26 may be positioned to overlie flexible member 24 with the externally curved portion of concave portion 32 engaging sidewall of cylindrical member 40 and opposing side edge portions 44 of other member 26 fixedly engage opposing side edge portions 46 of flexible member 24 snuggly positioning members 24 and 26 within cylindrical housing 40, as seen in FIGS. 5, 9, 10 and 11.

Cylindrical housing 40 is opened at both ends 41. Members 24, 26 are aligned with and extend out of each end of cylindrical housing 40, as seen in FIG. 5 and 6. With the corresponding edge portions 44, 46 fixedly secured to one another of members 24 and 26 upstream from at least a portion of concave portion 45 of another member 26 which overlies flexible member 24, this securement will position flexible member 24 to be unsecured at or proximate to a position where air flow 28 impacts flexible member 24 from other member 26 permitting flexible member 24 to act similarly to a cantilever beam as flexible member 24 deflects, as seen in FIGS. 5 and 10.

Figure 8:
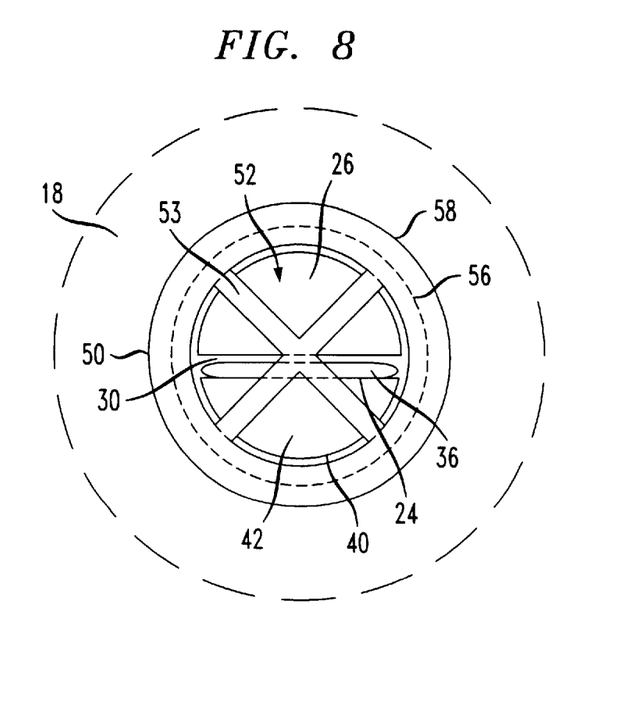
FIG. 8 is an elevational view of the apparatus of the present invention as seen along line 8—8 in FIG. 5.
Figure 9:
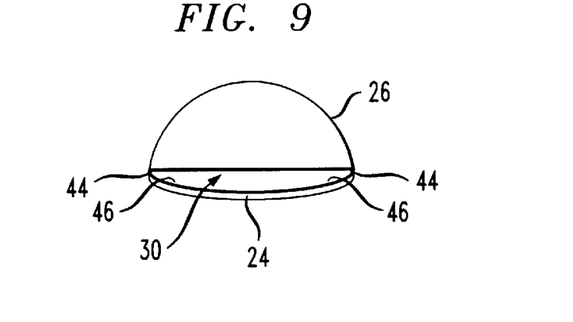
FIG. 9 is an enlarged view of the reed apparatus alone as seen along line 8—8 in FIG. 5.

The securement member 40 includes a housing member 48, as seen partially broken away in FIG. 5. Housing portion 48 is generally constructed of plastic or other suitable material and is constructed in generally a cylindrical shape. Cylindrical housing 40 has slightly smaller diameter and circumference to housing member 48 thereby creating a snug fit between cylindrical housing 40 and housing member 48 with cylindrical housing 40 inserted within housing member 48. Cylindrically shaped housing member 48 extends along flexible member 24 and other member 26 and has an end 50 positioned upstream from flexible and other members 24 and 26 and defines an aperture 52 which is aligned in the direction of the forced air stream 12, as seen in FIGS. 5 and 8. Opening 52 permits forced air stream 12 to enter the housing member 48 and permit air flow 28 to pass between flexible member and other member 24, 26 through space 30. A screening barricade number 53 is provided to block debris from air stream 12 from entering opening 20 and engaging and disabling flexible and other members 24, 26 with blocking space 30. Housing member 48 also defines another aperture 54 downstream from aperture 52 permitting air flow 28 from air stream 12 to pass out of housing member 48, as seen in FIGS. 5 and 7.

Referring to FIG. 5, a projecting member and another projecting member 56, 58 each project outwardly from cylindrically shaped housing member 48 in which members 56, 58 are spaced apart from one another and extend in a direction transverse to flexible and other members 24, 26 for engaging each side of porous material 18 of air filter 14. These projecting members 56, 58 each form an annular rim for engaging the porous material 18 that is positioned about housing member 48 securing housing member 48 to porous material 18.

The present invention includes a method for detecting blockage of porous medium 18 of air filter 14, in which air filter 14 is utilized to filter air within a forced air stream contained within an enclosure, duct or conduit. Air filter 14 generally extends in a direction transverse to the direction of air stream 12 as seen in FIG. 1.

The method includes the step of providing an opening 20 in porous medium 18 of air filter 14 as seen in FIGS. 1–4. This can be accomplished by many various ways including cutting, separating or even puncturing the porous medium 18 to create opening 20 which has a greater dimension than the openings that are provided by porous medium 18. Porous medium 18 defines opening 20 which extends through porous medium 18. Opening 20 extends generally in the direction of the oncoming forced air stream 12. Opening 20 can be of various shapes, however, in the present embodiment a generally circular cross section is utilized. As earlier discussed, air flow 28 from forced air stream 12 passes through opening 20.

As also discussed earlier, it is desirable to position opening 20 closer to an edge of air filter 14 than to a central portion of air filter 14, as seen in FIGS. 1 and 2. This can be expressed, if air filter 14 has an axis of symmetry S extending in the direction of air filter 14 transverse to forced air stream 12, that opening 20 will be positioned closer to an edge of filter 14 than to center C of axis of symmetry S.

The method includes the step of selecting flexible member or tongue 24 to overlie another member 26 which comprises the reed device discussed above and seen in FIG. 5. The flexible member 24 vibrates emitting a desired sound with flexible member 24 and another member 26 positioned to receive air flow 28 at a particular velocity. The selection of the dimensions of and composition of the particular tongue 24 that would be appropriate for emitting the desired sound when the conditions of a certain blockage of air filter 14 is attained with a certain velocity of air flow 28 will be discussed in more detail below.

The step of selecting a flexible member 24 also includes providing another member 26 which has a concave portion 32 for directing air flow 28 from forced air stream 12 to impact flexible member 24.

The method further includes the step of positioning at least a portion of each flexible and another members 24, 26 in communication with opening 20 in porous medium 18 to receive air flow 28 from forced air stream 12, as was discussed above.

The step of positioning includes securing the flexible and another member 24,26 together in which at least a portion of flexible and another members 24,26 are in spaced apart relationship, as earlier discussed in more detail. Positioning also includes securing flexible member at a position upstream of air flow 28 leaving a downstream end 47 of flexible member 24 unsecured, as seen in FIGS. 5,7 and 10. Additionally, positioning includes inserting flexible and another members 24, 26 into housing member 48. Housing 48 as described earlier, defines aperture 52 aligned in the direction of forced air stream 12 causing air flow 28 in housing member 48 to be received by members 24,26. Housing 48 also defines opposing aperture 54 to allow air flow 28 to pass out of housing 48.

The present method also includes in the step of positioning the providing of an engaging member 58 which projects from housing member 48 for engaging porous medium 18 of air filter 14 for securing housing member 48 to air filter 14, which has been discussed in more detail earlier.

The present invention provides a convenient and inexpensive way of alerting the maintenance personnel to replace the burdened air filter with a clean filter. The reed device which is comprised of members 24 and 26 as discussed above, provides an audible sound with air filter 14 burdened with debris.

The following discussion will set forth an example of how to go about selecting or designing the correct reed device or more precisely the tongue or flexible member 24 to provide a certain level of audible signal at a time that the porous medium 18 of air filter 14 has reached an undesirable blockage from the trapped debris from air stream 12.

First, for purposes of this example, the air stream and the confinement of the air stream must be evaluated and quantified. For this analysis the air stream will be confined in a duct having a cross sectional area of (A=1 square meter) in which the volumetric flow rate of the air stream in this duct will be (Q=1.5 cubic meters per second). The velocity of the free flowing air stream will be (V=Q/A) or V=1.5 meters per second.

Secondly, a clean air filter 14 as seen in FIG. 1, must be selected for placement within air stream 12. Air filter 14 as discussed above, may have various constructions such as their porous medium 18 being comprised of pressed paper for residential filters and interconnected polyester fibers covered with wire mesh for filters used for the more demanding higher velocity and volume commercial air streams.

For purposes of the following analysis, clean air filter 14 used in the air stream will provide a blockage to the free flowing air stream of 20%. In other words, clean air filter 14 blocks 20% of the crossectional area (A) of the duct.

At this juncture, a criteria for removal of the air filter and replacing it with a clean filter must be made. For purposes of this example, when 80% of the open cross section area of the duct is blocked by the combination of the filter itself and debris the filter has trapped, air filter 14 should be replaced. Thus, the reed device and more precisely the tongue or flexible member 24 must be designed or selected that has certain dimensions and composition that will emit an audible sound at a desired loudness to indicate the undesired 80% blockage of the duct has occurred.

As was discussed above, the reed device is positioned in opening 20 of air filter 14 and receives the oncoming air stream 12. Air or air flow 28 from air stream 12 passes through the reed device and exits on the downstream side of air filter 14. For purposes of this example, the cross sectional area of the reed will be selected to be about ¼' in diameter for a value which is approximately $4.9 \times 10^{-2}$ in$^2$ or approximately $3 \times 10^{-5}$ m$^2$.

With these initial criteria established, utilization of the conservation of momentum and energy and the application of Bernoulli's Equation $$\left\{ \frac{P_1}{\rho} + \frac{V_1^2}{2} + gZ_1 = \frac{P_2}{\rho} + \frac{V_2^2}{2} + gZ_2 \right\}.$$

Bernoulli's equation is an integration of Euler's equation along a streamline of steady flow. This equation will be applied to provide the modeling of tongue 24 of the reed device for this example. Bernoulli's Equation relates pressure, velocity and elevation of a flow where $P_1$ is the initial pressure of the oncoming air stream, $\rho$ the fluid density, in this instance air, $V_1$ the initial velocity of the oncoming air stream, g is gravitational acceleration and $Z_1$ the initial fluid elevation. Generally, the sum of these initial quantities, subscripted by $_1$, of the oncoming air stream 12 will equal the subsequent sum of the exit conditions, subscripted by $_2$, of the downward air stream 16 from air filter 14.

For purposes of this example, and the utilization of Bernoulli's Equation, one will assume the airflow in the system is less than 0.3 Mach, approximately 225 mph. Under this assumption, the air in the duct can be considered incompressible because the maximum density variation is less than 5%. In most cases of application of this modeling, the velocity of the air stream will be less than 225 mph and therefore compressibility of the air will not be taken into account. Additionally, the operating temperature range of air stream 12 will be between −50° C. to +80° C.

In modeling or designing the reed structure we will address the design of tongue 24 component of the reed device which will ultimately vibrate, see FIG. 10. As airflow 28 follows the contour of the concave portion 32 of flexible member 24 of the reed structure, a force as indicated by arrow F as seen in FIG. 10 is impacted on tongue 24 in a direction transverse to the direction the tongue 24 extends. Force F tends to push tongue 24 in the direction of force F and flex tongue 24 to 24'.

The forces being placed on tongue 24 as seen in FIG. 10 are as follows: in the downward direction it is force (F) which is the atmospheric pressure ($P_a$) times the surface area (A) of the tongue. In the opposing direction is ($K_x$), the force created by the fluid flow, which for our example is equal to ($-R_x$) the resultant force. The equilibrium of $K_x=-R_x$ is due to the equilibrium of the forces.

The surface force ($F_{sx}$) exerted on tongue 24 of the reed device based on the air flow 28 from air stream 12 which pushes downwardly onto tongue 24 from concave portion 32 of other member 26 of the reed device is calculated as follows:

$$F_{sx} = \int_{cs} u\rho V(\text{Vector}) \cdot dA(\text{Vector})$$

The force ($F_{sx}$) transverse to the direction to which the tongue 24 extends is the integration over the control surface (cs) of the product of the free air stream velocity (u); the air density ($\rho$) of approximately 1.16 kg/m³; the velocity vector (V) which is perpendicular to tongue 24; and the derivative of the area vector (dA) of the surface of tongue 24 or the cross sectional area of the reed device. This can be represented also as follows:

$$F_{sx} = P_a A + R_x = \int_{AI} u\rho V(\text{Vector}) \cdot dA(\text{Vector})$$

$$= \int_{AI} u\{-|\rho V_1 dA\} =$$

$$= 1.5 \text{ m/s } |(1.16 \text{ kg/m}^3)(1.5 \text{ m/s})(3 \times 10^{-5} \text{ m}^2)|$$

$$= 7.8 \times 10^{-5} \text{ N (Newtons)}$$

$$R_x = -P_a A - F_{sx} \quad \& \quad K_x = -R_x$$

$$\therefore F_{net} = K_x - P_a A$$

$$F_{net} = P_a A + 7.8 \times 10^{-5} \text{ N} - P_a A$$

$$F_{net} = 7.8 \times 10^{-5} \text{ N}$$

The net force "$F_{net}$" is the force the unrestricted flow of the air stream imparts on tongue 24 of the reed device with no flow restrictions in the conduit or duct.

At this juncture, clean filter 14 that is being used, as discussed earlier, reduces the cross sectional area of the conduit in which air stream 12 is flowing by 20%. With this, we can now calculate the velocity (VR) of the air stream through the reed device with air filter 14 in a clean unburdened condition.

$$V_R = \frac{Q}{A} = \frac{1.5 \text{ m}^3/\text{sec}}{0.8 \text{ m}^2} = 1.875 \text{ m/sec.}$$

As one can see, the free flowing velocity of the air stream was 1.5 m/sec, but with clean air filter 14 in the duct the cross sectional area of the duct is reduced thereby increasing the velocity from 1.5 m/sec. to 1.875 m/sec. As a result, the force now applied to tongue 24 of the reed with the presence of a clean air filter 14 with the increased velocity of 1.875 m/sec. is as follows:

$$F_{sx} = u\{-|\rho V_1 dA|\}$$

$$= 1.875 \text{ m/sec } |(1.16 \text{ kg/m}^3)(1.875 \text{ m/sec})(3 \times 10^{-5} \text{ m}^3)|$$

$$= 1.2 \times 10^{-4} \text{ N (Newtons)}$$

It is clear, this force now exerted on flexible member or tongue 24 ($1.2 \times 10^{-4}$ N) is larger than the force (F) imparted onto tongue 24 of the reed where there is no blockage or restriction in air stream 12 flow which was $7.8 \times 10^{-4}$ N.

Progressing with this analysis, one will now select the undesired amount of blockage for the duct to be 80% blockage of the free flow passageway. This will be the point at which filter 14 must be replaced. The velocity ($V_R$) of the flow 28 of the air received by the reed will be dramatically increased and likewise the force (F) that is imparted on tongue 24 of the reed in a direction transverse to the tongue 24 will be dramatically increased (at 80% blockage of duct).

$$V_R = \frac{Q}{A} = \frac{1.5 \text{ m}^3/\text{sec}}{0.2 \text{ m}^2} = 7.5 \text{ m/sec.}$$

$$F_{sx} = 7.5|(1.16 \text{ kg/m}^3)(7.5 \text{ m/sec})(3 \times 10^{-5} \text{ m}^2)| = 1.96 \times 10^{-3} \text{ N}$$

As one will note, this force ($F_{sx}$) with an 80% blocked duct will be approximately twenty five times (25×) greater than the force imparted to tongue 24 with no restriction in the duct and sixteen times (16×) greater when a clean air filter 14 is present.

The analysis shows that as the air filter 14 becomes more loaded with debris, the force (F) exerted on tongue 24 of the reed is increased significantly. Tongue 24, as described above, acts as a cantilever beam and tongue or flexible member 24 will deflect as the force exerted on flexible member 24 increases. The stiffer the beam, the more force (F) it will take to deflect it to initiate the tongue to vibrate and emit sound. On the other hand, the softer the beam the less force (F) it will take to initiate the deflection of tongue 24 away from other member 26 and initiate vibration of flexible member 24 and thereby emit sound. The force (F) to deflect a cantilever beam is normally expressed as follows:

$$F_{beam} = K\delta$$

Where ($\delta$) is the amount of the deflection and (K) is the spring stiffness.

The vibration of flexible member 24 is the result of the dynamic action of flexible member 24 overcoming the deflecting force (F) imparted by air flow 28. As a result, the deflecting force (F) is overcome by the resilience of flexible member 24 pushing flexible member 24 toward other member 26. These forces initiate the vibration of flexible member 24.

As flexible member 24 restricts the space between itself and another member 26, the air pressure between the members 24, 26 increases assisting pushing flexible member 24 toward the original deflected direction. This dynamic condition continues the flexible member 24 to vibrate.

Thus, this movement of flexible member 24 closer to other member 26 creates a higher pressure of the air between the two members 24, 26 and as flexible member 24 deflects away from other member 26 the air pressure between the members is reduced. This cyclical increase and decrease of air pressure creates a sound wave. As the velocity of air flow 28 increases, force (F) that impacts flexible member 24 increases. As force (F) increases the cyclical amplitude of flexible member 24 increases thereby increasingly emitting a louder audible tone.

Since the flow of air stream 12 in the duct will be generally considered fixed, one can select the frequency (f) at which tongue 24 will resonate. Keeping in mind that the selected frequency (f) will be readily discerned by the maintenance personnel either by listening to the emitted audible tone or utilizing well known sound pressure level meters. In utilizing the sound pressure level meters, the task of perceiving the audible tone signal for the loaded filter 14 can be accomplished from remote locations.

$$f = \left[\frac{0.5596}{l^2}\right]\left[\frac{EK}{\rho}\right]^{0.5}$$

where l=length of the tongue in (cm)
$\rho$=density of the tongue in (gm/cm$^3$)
E=Modulus of Elasticity (of the tongue)
K=Radius of gyration (which is an expression of the cross section thickness of the tongue in the plane of bending, in this example $$K = \frac{thickness}{12}$$

for a rectangular cross section)

0.5596=is a conversion factor to convert into centimeters
Now taking ($\delta$) deflection from above, it can now be expressed as:

$$\delta = \frac{F_{sx}l}{EA}$$

in which (A) is the cross sectional area of the tongue. Most often the tongue is rectangular in cross section therefore K=a/12 where a=tongue thickness in (cm).

At this point, one should select the material in which to construct tongue 24. For this example, the material selected will be brass which has a density ($\rho$)=8400 kg/m$^3$ and the modulus of elasticity (E)=100 GPa (gigapascals) 1 psi (pounds per square inch pressure)=6894.76 Pa. Other materials may be selected that have desirable characteristics of non-corrosion and durability.

At this point, one can select the thickness (a) in centimeters you wish tongue 24 of the reed to have, e.g. a=0.08 cm=approx. 1/32 of an inch which would be relatively easy to produce. Then, the radius of gyration (K) is as follows:

K=0.08 cm/12=6.6×16$^{-3}$ cm

At this point, one needs to select a desired frequency (f) to resonate the tongue of the reed at in producing an audible signal indicating the blockage of the duct when it reaches 80%. For this example 20,000 Hz will be the frequency. This frequency will be selected based on the working environment and the level desired that would be readily perceptible to the personnel to indicate the time for the air filter to be replaced.

Now, one can calculate how long (l) the tongue 24 of the reed will be with these parameters.

$$20,000 = \left\{\frac{0.5596}{l^2}\right\}\left\{\frac{(100 \times 10^9 \text{ N/m}^2) \; 6.6 \times 10^{-5} \text{ m}}{8400 \text{ kg/m}^3}\right\}^{0.5}$$

l=2.8×10$^{-2}$ m≈1.1 inches

Now, one can resolve the width of the tongue from the following:

$$K = \frac{EA}{l}$$

where (K) is the spring stiffness of tongue 24, (E) the modulus of elasticity and (l) the length of the tongue. Iterative calculations can now be made to achieve the width of tongue 24 that is desirable.

Thus, a 20,000 Hz frequency sound will be generated with 80% blockage of the duct. The force on tongue 24 of the reed will be 1.96×10$^{-3}$ N. Tongue 24 will be constructed of brass with a thickness (a=0.08 cm) and the length of the tongue will be l=2.8×10$^{-2}$ m.

Under this example, one can now choose a ($\delta$) deflection of tongue 24 that would be desirable to obtain in these circumstances or a tongue width or vice versa.

F=K$\delta$

As mentioned above, the force (F) on a cantilever beam or in this instance tongue 24 of a reed equals the spring stiffness (K) times the deflection ($\delta$). Thus, $$\delta = \frac{F}{K}\frac{EA}{l}$$

$$= \frac{E(thickness)(width)}{l}$$

where all of the above are now known, the deflection ($\delta$) will be as follows:

($\delta$)=0.0048m=approx. 3/16"

This may be a little more deflection than one may want for this reed tongue 24.

With the value of ($\delta$) deflection being 0.0048 m, we can insert the known values into the following:

$$F_{sx} = \frac{EA}{l}\delta$$

$$1.96 \times 10^{-3} \text{ N} = \frac{(100 \times 10^9 \text{ N/m}^3)(6.6 \times 10^{-5} \text{ m})(width)(0.0048)}{2.8 \times 10^{-2} \text{ m}}$$

width = 1.7×10$^{-7}$ m

This would be a very narrow dimension for tongue 24. As a result, a width can be selected which is easy to manufacture of 0.0043 m. With this width, the deflection ($\delta$) will be 1.7×10$^{-9}$ m.

Thus, for the example, with an 80% blockage of the conduit of one square meter, the oncoming air stream having a 1.5 meter$^3$/sec volumetric flow, a reed tongue 24 made of brass with the length (l) of 2.8×10$^{-2}$ m, thickness (a) of 0.08 cm or 0.08×10$^{-2}$ m and width (w) 4.8×10$^{-3}$ m or 0.48×10$^{-2}$ m will emit a 20,000 Hz sound with a deflection of 1.7×10$^{-9}$ m.

Working with this example, will provide the mechanism and procedure to design or select reed tongue 24 which will emit a sound at a desired level, with a predetermined undesirable filter blockage. The sound signals the need for replacement of air filter 14 for the particular forced air system at hand.

While a description of the preferred embodiments of the invention has been given, it shall be appreciated that many variations can be made thereto without departing from the scope of the invention as set forth in the appended claims.

What is claimed is:

1. An apparatus for detecting blockage of a porous medium of an air filter utilized to filter air within a forced air stream contained within an enclosure and the air filter extends in a direction transverse to a direction of the forced air stream, comprising:

an opening in the porous medium, which opening extends through the porous medium through which an air flow from the forced air stream passes; and a flexible member positioned within the air flow from the forced air stream that passes through the opening and received by flexible member causing the flexible member to vibrate and emit a desired audible sound in response to a certain velocity of the air flow.

2. The apparatus of claim 1 in which the porous medium is pressed paper.

3. The apparatus of claim 1 in which the porous medium is polyester fibers.

4. The apparatus of claim 1 in which the air filter has a dimension that is greater in the direction transverse to the forced air stream than a dimension of the air filter that extends in the direction of the forced air stream.

5. The apparatus of claim 1 in which the opening that extends through the porous medium extends along in the direction of the forced air stream.

6. The apparatus of claim 1 in which the opening is positioned closer to an edge of the air filter than to a central portion of the air filter.

7. The apparatus of claim 1 in which the air filter has an axis of symmetry that extends in the direction transverse to the direction of the forced air stream.

8. The apparatus of claim 7 in which the opening is positioned closer to an external edge of the filter than to a center of the axis of symmetry.

9. The apparatus of claim 1 in which the flexible member is longer in a dimension that extends in a direction of the air flow from the forced air stream than a dimension of the flexible member that extends in the direction of the air filter transverse to the forced air stream.

10. The apparatus of claim 9 in which the flexible member has a generally rectangular cross sectional shape that extends transverse to the direction of the forced air stream.

11. The apparatus of claim 1 includes another member in which the flexible member overlies the other member and is positioned within the air flow.

12. The apparatus of claim 11 in which the other member extends generally along a dimension of the flexible member in the direction of the air flow from the forced air stream and in which at least a portion of the flexible and other members are spaced apart from one another along at least the dimension of the flexible member and in a direction transverse to the direction of the air flow from the forced air stream.

13. The apparatus of claim 12 in which the other member has a concave portion defined by the other member, positioned to have an open portion of the concave portion face the flexible member for directing air from the air flow in a direction transverse to and impacting the flexible member.

14. The apparatus of claim 13 in which the concave portion directs the air flow to impact flexible member downstream from a front end of the flexible member.

15. The apparatus of claim 13 includes a securement member for securing the flexible member and the other member in fixed relationship to one another upstream in the air flow from at least a portion of the concave portion of the other member that overlies the flexible member where the air flow impacts the flexible member proximate an unsecured portion of the flexible member.

16. The apparatus of claim 15 in which the securement member includes a housing member that extends along the flexible member and the other member in which the housing has an end positioned upstream of the air flow from the concave portion of the other member in which the end defines an aperture aligned in the direction of the forced air stream causing the air flow in the housing and to be received by the flexible member and another member and in which the housing defines another aperture downstream in the air flow from the aperture permitting the air flow from the forced air stream to pass out of the housing member.

17. The apparatus of claim 16 in which the housing member includes a projecting member that extends outwardly from the housing member and in a direction transverse to the flexible and another member for engaging the porous medium of the air filter.

18. The apparatus of claim 17 in which the housing member includes another projecting member spaced apart from the projecting member and extending outwardly from the housing member and in a direction transverse to the flexible and other members for engaging the porous medium of the air filter.

19. The apparatus of claim 1, further comprising a housing for the flexible member and at least two annular rims positioned around the housing for engaging the porous material of the air filter and positioning at least a portion of the housing within the opening.

20. The apparatus of claim 1 in which the flexible member is constructed of one of brass, aluminum, stainless steel or bronze.

21. A method for detecting blockage of a porous medium of an air filter utilized to filter air within a forced air stream contained within an enclosure and the air filter extends in a direction transverse to a direction of the forced air stream, including the steps of:

providing an opening in the porous medium of the air filter in which the opening extends through the porous medium in the direction of the forced air stream through which an air flow from the forced air stream passes;

selecting a flexible member in which the flexible member vibrates emitting a desired audible sound with the flexible member positioned to receive the air flow at a particular velocity; and positioning at least a portion of the flexible member in communication with the opening in the porous medium to receive an air flow from the forced air stream.

22. The method of claim 21 the step of providing an opening includes positioning the opening closer to an edge of the air filter than to a central portion of the filter.

23. The method of claim 21 the step of providing an opening includes the air filter having an axis of symmetry extending in the direction of the air filter transverse to the forced air stream and positioning the opening closer to an edge of the air filter than a center of the axis of symmetry.

24. The method of claim 21 the step of providing an opening includes making the opening have generally a circular cross section.

25. The method of claim 21 the step of selecting a flexible member includes selecting the composition and dimensions of the flexible member.

26. The method of claim 21 in which the step of selecting includes selecting another member in which the flexible member overlies the other member; and in which the step of positioning includes positioning at least a portion of the other member in communication with the opening to receive the air flow from the forced air stream.

27. The method of claim 26 the step of selecting a flexible member includes providing the another member with a concave portion for directing the air flow from the forced air stream to impact the flexible member.

28. The method of claim 26 the step of positioning includes securing the flexible and another members together in which at least a portion of the flexible and another member are in spaced apart relationship.

29. The method of claim 28 in which the step of securing includes securing the flexible member at a position upstream of the air flow leaving a downstream end of the flexible unsecured.

30. The method of claim 28 in which the step of positioning includes inserting the flexible and another members into a housing member that has an aperture defined by the housing member aligned in the direction of the forced air stream causing the air flow in the housing member to be received by the flexible and other members and has an opposing opening defined by the housing member to allow the air flow to pass out of the housing member.

31. The method of claim 30 in which the step of positioning includes engaging a member that projects from the housing member with the porous material of the air filter securing the housing member to the air filter.

32. An apparatus comprising:

a porous medium that has a surface that is downwind of an air flow;

an opening in the porous medium;

a device positioned within the opening and at least partially within the air flow, such that the device emits an audible sound when the air flow is at least partially blocked within the porous medium.

33. The apparatus of claim 32, wherein the porous medium is disposed in an air filter.

34. A method comprising the steps of:

providing an opening in a porous medium that has a surface that is downwind of an air flow;

placing a device in the opening such that the device emits an audible sound when the air flow is at least partially blocked within the porous medium.

35. The method of claim 34, wherein the porous medium is disposed in an air filter.

* * * * *